United States Patent
Humphreys et al.

(10) Patent No.: US 8,118,873 B2
(45) Date of Patent: Feb. 21, 2012

(54) TOTAL JOINT REPLACEMENT

(75) Inventors: Steven C. Humphreys, Chattanooga, TN (US); Scott D. Hodges, Ooltewah, TN (US); Eric C. Lange, Collierville, TN (US); Danny Braddock, Jr., Germantown, TN (US); Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1072 days.

(21) Appl. No.: 12/015,176

(22) Filed: Jan. 16, 2008

(65) Prior Publication Data

US 2009/0182429 A1    Jul. 16, 2009

(51) Int. Cl.
    A61F 2/44    (2006.01)
(52) U.S. Cl. .................................. 623/17.16
(58) Field of Classification Search ..... 623/17.11–17.16
    See application file for complete search history.

(56) References Cited

U.S. PATENT DOCUMENTS

| | | |
|---|---|---|
| 4,946,378 A | 8/1990 | Hirayama |
| 5,443,513 A | 8/1995 | Moumene |
| 5,702,450 A | 12/1997 | Bisserie |
| 5,928,284 A | 7/1999 | Mehdizadeh |
| 6,402,785 B1 | 6/2002 | Zdeblick et al. |
| 6,491,724 B1 * | 12/2002 | Ferree ...................... 623/17.11 |
| 6,572,653 B1 | 6/2003 | Simonson |
| 6,607,557 B1 | 8/2003 | Brosnahan et al. |
| 6,958,077 B2 | 10/2005 | Suddaby |
| 6,984,246 B2 | 1/2006 | Huang |
| 7,052,515 B2 | 5/2006 | Simonson |
| 7,066,960 B1 * | 6/2006 | Dickman ................... 623/17.16 |
| 7,128,761 B2 | 10/2006 | Kuras et al. |
| 2003/0055427 A1 * | 3/2003 | Graf ................................ 606/61 |
| 2003/0120348 A1 | 6/2003 | Brosnahan |
| 2004/0181285 A1 | 9/2004 | Simonson |
| 2004/0186576 A1 | 9/2004 | Biscup et al. |
| 2004/0220672 A1 | 11/2004 | Shadduck |
| 2004/0249462 A1 | 12/2004 | Huang |
| 2005/0043800 A1 | 2/2005 | Paul et al. |
| 2005/0055099 A1 | 3/2005 | Ku |
| 2005/0131540 A1 | 6/2005 | Trieu |
| 2005/0171610 A1 * | 8/2005 | Humphreys et al. ....... 623/17.15 |
| 2005/0192671 A1 | 9/2005 | Bao et al. |
| 2005/0228500 A1 | 10/2005 | Kim et al. |
| 2005/0251261 A1 | 11/2005 | Peterman |
| 2005/0267581 A1 | 12/2005 | Marnay et al. |

(Continued)

FOREIGN PATENT DOCUMENTS

WO    2005077304 A    8/2005

(Continued)

OTHER PUBLICATIONS

International Search Report, Jun. 1, 2009.

*Primary Examiner* — Thomas C. Barrett
*Assistant Examiner* — David Bates (57) ABSTRACT

An artificial vertebral joint for interposition between a superior vertebra and an inferior vertebra comprises a pair of bilateral joint subcomponents. Each joint subcomponent includes a superior component including a superior vertebra engaging surface and an inferior component including an inferior vertebra engaging surface. Each joint subcomponent further includes a spacer extending between the superior component and the inferior component. The spacer includes a first modulus of elasticity and a second modulus of elasticity. The first modulus transitions to the second modulus with a gradient change.

25 Claims, 10 Drawing Sheets

U.S. PATENT DOCUMENTS

| | | |
|---|---|---|
| 2005/0273178 A1 | 12/2005 | Boyan et al. |
| 2005/0283242 A1 | 12/2005 | Zucherman et al. |
| 2006/0025862 A1 | 2/2006 | Villiers et al. |
| 2006/0036325 A1 | 2/2006 | Paul et al. |
| 2006/0064170 A1 | 3/2006 | Smith et al. |
| 2006/0069437 A1 | 3/2006 | Weber |
| 2006/0085076 A1 | 4/2006 | Krishna et al. |
| 2006/0095133 A1 | 5/2006 | Eisermann et al. |
| 2006/0106459 A1 | 5/2006 | Truckai et al. |
| 2006/0116768 A1 | 6/2006 | Krueger et al. |
| 2006/0142860 A1 | 6/2006 | Navarro et al. |
| 2006/0178744 A1 | 8/2006 | de Villiers et al. |
| 2007/0043443 A1 * | 2/2007 | Snell et al. ............... 623/17.13 |
| 2007/0050033 A1 | 3/2007 | Reo |
| 2007/0050037 A1 | 3/2007 | Snell |

FOREIGN PATENT DOCUMENTS

| | | |
|---|---|---|
| WO | 2008005252 A | 1/2008 |
| WO | 2008094881 A | 8/2008 |

* cited by examiner

TOTAL JOINT REPLACEMENT

TECHNICAL FIELD

Embodiments of the invention relate generally to devices for accomplishing spinal surgery, and more particularly in some embodiments, to spinal arthroplasty devices capable of being placed posteriorly into the vertebral disc space. Various implementations of the invention are envisioned, including use in total spine arthroplasty replacing, via a posterior approach, both the disc and facet functions of a natural spinal joint.

BACKGROUND

Figure 1:
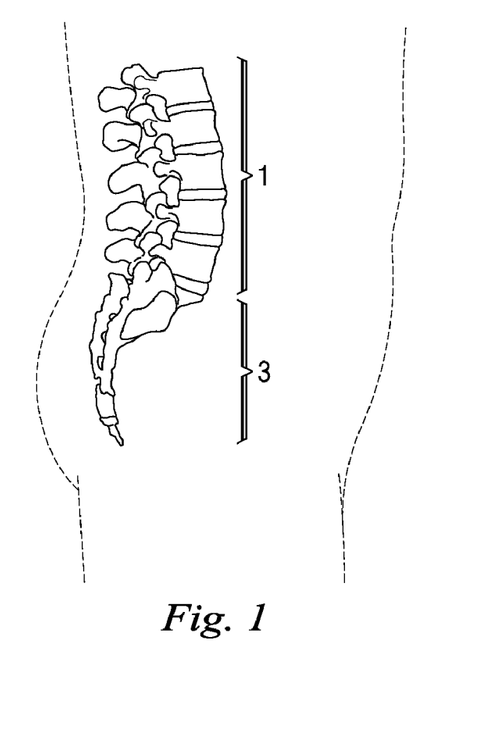
FIG. 1 is a side elevation schematic view of the lumbar spinal and the sacrum regions of a human spinal column.

The spine is a generally flexible column that can take tensile and compressive loads, allows bending motion and provides a place of attachment for ribs, muscles and ligaments. Generally, the spine is divided into three sections: the cervical, the thoracic and the lumbar spine. FIG. 1 illustrates schematically the lumbar spinal 1 and the sacrum regions 3 of a healthy, human spinal column. The sections of the spine are made up of individual bones called vertebrae, and the vertebrae are separated by intervertebral discs which are situated therebetween.

Figure 2:
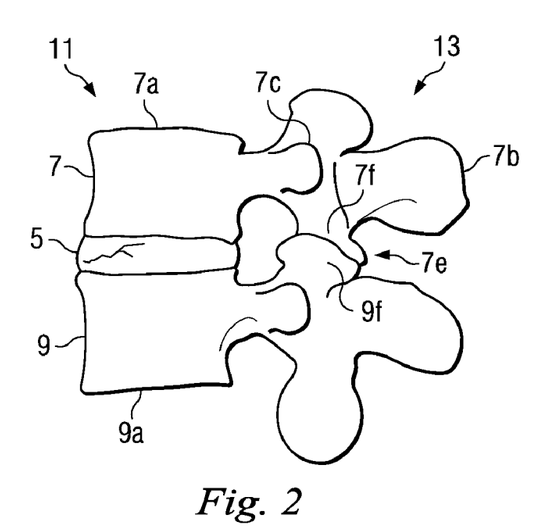
FIG. 2 is a detailed perspective view showing a portion of the right side of the lumbar vertebrae shown in FIG. 1 with a damaged disc disposed between two vertebrae.
Figure 3:
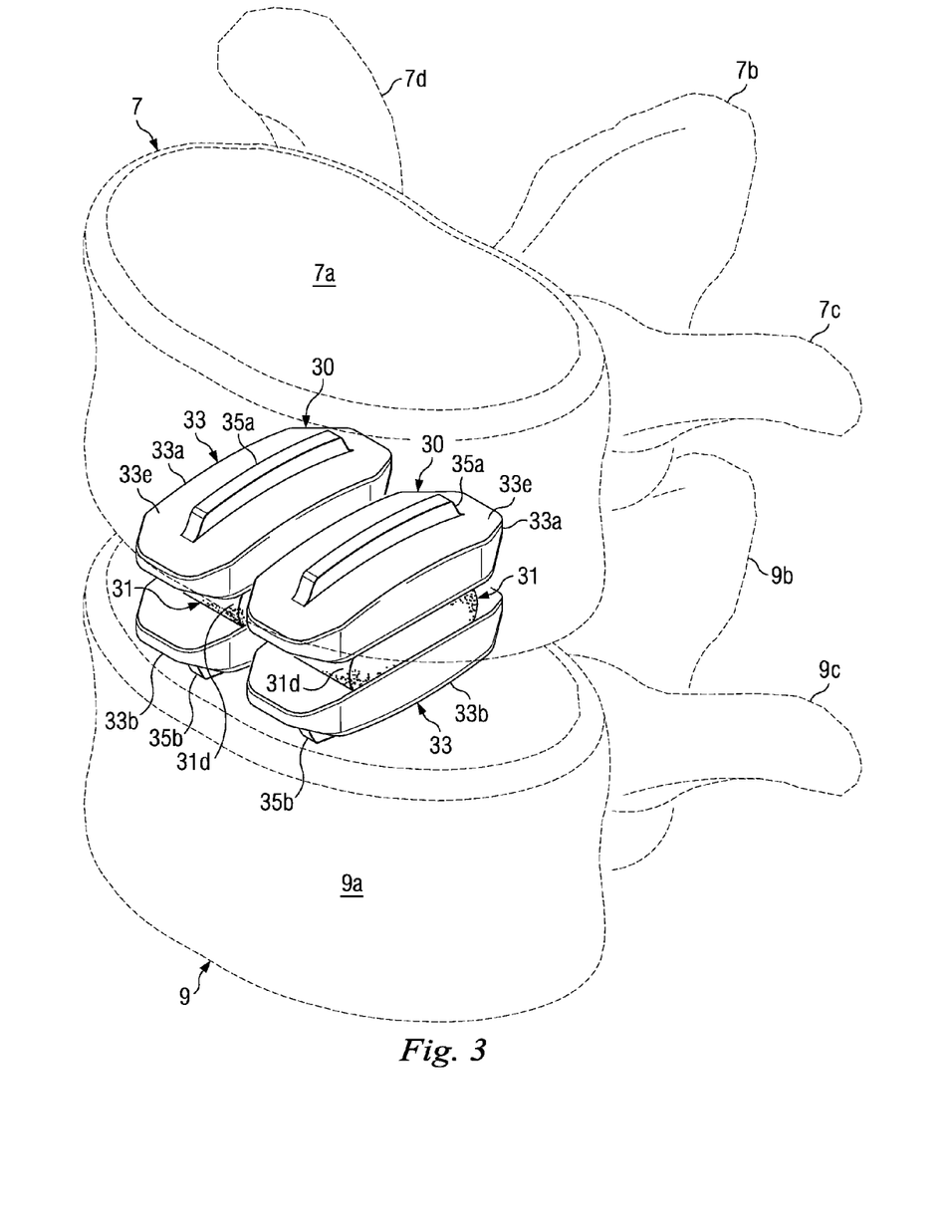
FIG. 3 is a perspective view of a portion of a lumbar spine showing a first embodiment of an artificial intervertebral joint constructed according to the principles of the disclosure.

FIG. 2 illustrates a portion of the right side of a lumbar spinal region with a damaged intervertebral disc 5 disposed between two adjacent vertebrae 7, 9. The lumbar spinal region includes an anterior section 11 and a posterior section 13. In any given joint, the top vertebra may be referred to as the superior vertebra and the bottom one as the inferior vertebra. Each vertebra comprises a generally cylindrical body 7a, 9a, which is the primary weight bearing area of the vertebrae 7, 9, respectively. Vertebra 7 further includes a spinous process 7b and transverse processes 7c, 7d (7b and 7c are visible, for example, in FIGS. 2-3 and 7d is visible, for example, in FIG. 3). Similarly, the vertebra 9 includes a spinous process 9b and transverse processes 9c, 9d (not shown). The processes, among other functions, provide areas for muscle and ligament attachment. A facet joint 7e is located between articular processes 7f, 9f of the superior and inferior vertebrae 7, 9, respectively.

Intervertebral discs function as shock absorbers and as joints. They are designed to absorb the compressive and tensile loads to which the spinal column may be subjected while at the same time allowing adjacent vertebral bodies to move relative to each other a limited amount, particularly during bending (flexure) of the spine. Thus, the intervertebral discs are under constant muscular and/or gravitational pressure and generally are the first parts of the lumbar spine to show signs of "wear and tear".

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

One surgical procedure for treating these conditions is spinal arthrodesis (i.e., spine fusion), which has been performed both anteriorly and/or posteriorly. The posterior procedures include in-situ fusion, posterior lateral instrumented fusion, transforaminal lumbar interbody fusion ("TLIF") and posterior lumbar interbody fusion ("PLIF"). Solidly fusing a spinal segment to eliminate any motion at that level may alleviate the immediate symptoms, but may result in further deterioration of the adjacent levels over time. Maintaining motion at the joint, for example through the use of an artificial disc, may be a solution of some patients. However, none of the known devices or methods provide the advantages of the embodiments of the present disclosure.

Accordingly, the foregoing shows there is a need for improved spinal arthroplasty devices that avoid the drawbacks and disadvantages of the known implants.

SUMMARY

In one embodiment, an artificial vertebral joint for interposition between a superior vertebra and an inferior vertebra comprises a pair of bilateral joint subcomponents. Each joint subcomponent includes a superior component including a superior vertebra engaging surface and an inferior component including an inferior vertebra engaging surface. Each joint subcomponent further includes a spacer extending between the superior component and the inferior component. The spacer includes a first modulus of elasticity and a second modulus of elasticity. The first modulus transitions to the second modulus with a gradient change.

In a second embodiment, an artificial vertebral joint for interposition between a superior vertebra and an inferior vertebra comprises a pair of bilateral joint subcomponents. Each joint subcomponent includes a superior component including a superior vertebra engaging surface and a superior spacer engaging surface. Each joint subcomponent further includes an inferior component including an inferior vertebra engaging surface and an inferior spacer engaging surface. Each joint subcomponent further includes a spacer extending between the superior component and the inferior component. The spacer includes a mesh container and a core contained within the mesh container.

In a third embodiment, a method for implanting an artificial vertebral joint between superior and inferior vertebrae comprises creating an access path to an intervertebral disc space between the superior and inferior vertebrae with a posterior transforaminal approach. The method further includes inserting a superior component of the artificial vertebral joint into the intervertebral disc space. The superior component includes a superior posterior element. The method also includes inserting an inferior component of the artificial vertebral joint into the intervertebral disc space. The inferior component includes an inferior posterior element. The method further includes inserting a spacer of the artificial vertebral joint into the intervertebral disc space. The spacer comprises an elastomeric material. The method also includes arranging the superior and inferior posterior elements to extend posteriorly from the intervertebral disc space and placing the superior posterior element into articulating engagement with the inferior posterior element.

Additional and alternative features, advantages, uses and embodiments are set forth in or will be apparent from the following description, drawings, and claims.

BRIEF DESCRIPTION OF THE DRAWINGS

In the figures referenced above, it is understood that the scale and location of the artificial intervertebral joint systems with respect to the vertebrae may be modified.

DESCRIPTION

The drawings illustrate various embodiments of an artificial intervertebral joint for replacing an intervertebral disc or the combination of an intervertebral disc and at least one corresponding facet joint. Various embodiments of the artificial intervertebral joint according to the principles of the disclosure may be used for treating any of the problems that lend themselves to joint replacement including particularly, for example, degenerative changes of the lumbar spine, post-traumatic, discogenic, facet pain or spondylolisthesis and/or to maintain motion in multiple levels of the lumbar spine.

Figure 4:
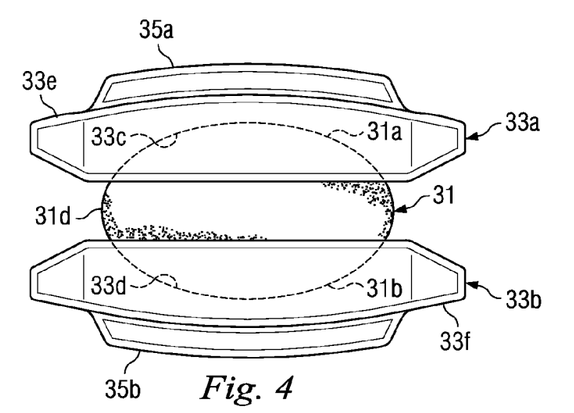
FIG. 4 is a side view of the artificial intervertebral joint illustrated in FIG. 3.

FIGS. 3-6 illustrate a first exemplary embodiment of an artificial intervertebral joint. As illustrated in FIGS. 3-4, each joint is composed of a pair of arthroplasty subcomponents 30, each of which has a spacer 31 and a retaining portion 33. The retaining portion 33 includes a superior component 33a and an inferior component 33b. In the example illustrated in FIG. 3, the superior component 33a is superior to (above) the inferior component 33b and the spacer 31 is situated therebetween. Although the artificial intervertebral joint according to this exemplary embodiment includes a pair of arthroplasty subcomponents, it should be understood that alternative embodiments may be implemented such that an artificial intervertebral joint includes a single arthroplasty subcomponent or more than two arthroplasty subcomponents. It should also be understood that alternative embodiments may also be carried out with arthroplasty components of unequal sizes. In the exemplary embodiment illustrated in FIGS. 3-4, the spacer 31 is a separate component which is inserted between the superior component 33a and the inferior component 33b. However, it should be understood that in some alternative embodiments the spacer may be integrally formed with or integrated into one or both of the superior component and the inferior component.

The superior component 33a includes a superior vertebra engaging surface 33e structured to engage the superior vertebral body 7a. Likewise, the inferior component 33b includes an inferior vertebra engaging surface 33f structured to engage the inferior vertebral body 9a. Additionally, the superior component 33a includes an optional superior keel 35a extending from the superior vertebra engaging surface 33e and the inferior component 33b includes an optional inferior keel 35b extending from the inferior vertebra engaging surface 33f to stabilize the arthroplasty subcomponent 30. The superior keel and the inferior keel may include holes so as to promote bone ingrowth. Additionally, the superior keel may include a catch so as to help further secure the superior component to the superior vertebra 7.

In alternative embodiments, the width and height of one or both of the keels may vary. In other embodiments, the lower portion of one or both of the keels may be narrower than the taller portion of one or both of the keels. In other embodiments, one or both of the keels may taper or have an undulating wave form. In other embodiments, one or both of the keels may have parts that are of different heights.

In the various embodiments of this disclosure, the superior component and/or the inferior component may be rigid, and may be formed of any suitable biocompatible materials including metal such as cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); TECAMAX; polysulfone; polyetherimide; polyimide; ultra-high molecular weight polyethylene (UHMWPE); and/or cross-linked UHMWPE. The various components comprising the superior component and the inferior component may be formed of different materials.

Figure 5:
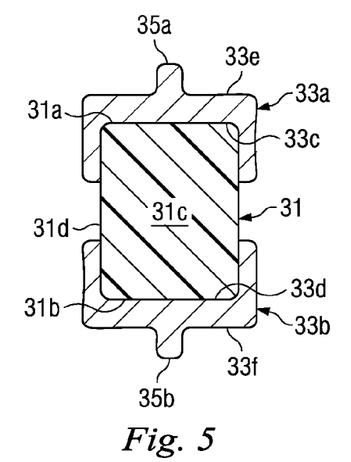
FIG. 5 is a cross-sectional view of the artificial intervertebral joint illustrated in FIGS. 3-4.
Figure 6:
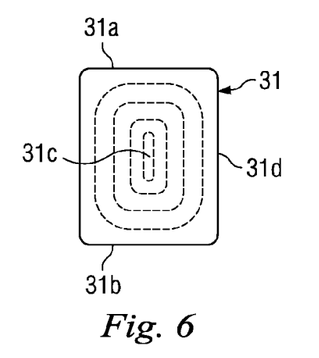
FIG. 6 is a front view of a spacer used in the artificial intervertebral joint constructed according to the first embodiment of the disclosure.

In this embodiment, the spacer 31 is made of an elastomeric material such as polyurethane, silicone, silicone polyurethane copolymers, polyolefins, such as polyisobutylene rubber and polyisoprene rubber, neoprene rubber, nitrile rubber, vulcanized rubber and combinations thereof. Certain portions of the implant, such as lower modulus regions, layers, or areas may be formed of more deformable or compliant materials including soft elastomers and polymeric gels. Additionally, as illustrated in FIGS. 5-6, the spacer 31 includes an interior 31c and a surface 31d. The interior 31c is located at the interior of the spacer 31 and the surface 31d is located at the exterior of the spacer 31. The interior 31c has an interior modulus and the surface 31d has a surface modulus that differs from the interior modulus. As shown in FIG. 6, there is a gradual gradient change from the surface modulus to the interior modulus. The surface modulus may be higher than the interior modulus, resulting in the surface being harder than the interior. Alternatively, the surface modulus may be lower than the interior modulus, resulting in the surface being softer than the interior. The spacer 31 may also include a surface coating or a hardening treatment.

Gradual changes in gradient may be achieved through molding methods, including injection molding methods.

Within a spacer formed of an otherwise homogeneous material, the modulus of elasticity may be varied by varying the amount and type of chemical crosslinking. The gradient changes may also result from combining or dispersing additional materials in varying amounts throughout an otherwise homogeneous material to achieve a desired combined or blended modulus. Modulus gradation can also result from the use of reinforcing materials. Furthermore, variations in gradation may be achieved through physical features such as changes in implant thickness, surface patterns, material porosity, or material voids.

As illustrated in FIG. 3, the superior component 33a and the inferior component 33b are situated between two adjacent vertebrae 7, 9. More particularly, the superior component 33a may be situated along an inferior surface of the superior vertebral body 7a, and the inferior component 33b may be situated on a superior surface of the inferior vertebral body 9a. However, it should be understood by one of ordinary skill in the art that the superior component and the inferior component are not limited to such an arrangement, and may be oriented in different positions and/or shaped differently than what is illustrated herein.

In the various embodiments of this disclosure, the surfaces of the superior component and the inferior component of the arthroplasty that contact the remaining endplates of the vertebrae may be coated with a beaded material or plasma sprayed to promote bony ingrowth and a firm connection therebetween. In particular, the surface to promote bone ingrowth may be a cobalt chromium molybdenum alloy with a titanium/calcium/phosphate double coating, a mesh surface, or any other effective surface finish. Alternatively or in combination, an adhesive or cement such as polymethylmethacrylate (PMMA) may be used to fix all or a portion of the implants to one or both of the endplates.

In this embodiment, the superior component 33a and the inferior component 33b are structured so as to retain the spacer 31 therebetween. For example, in the case of the spacer 31 with two convex surfaces 31a, 31b, illustrated best in FIGS. 4-6, each of the superior component 33a and the inferior component 33b has a concave surface 33c, 33d, respectively, which defines a space within which the spacer 31 may be retained. In the exemplary embodiment shown in FIGS. 4-5, the superior convex surface 31a of the spacer 31 fits within the concavity defined by the non-spherical concave surface 33c of the superior component 33a, and the inferior convex surface 31b of the spacer 31 fits within the concavity defined by the non-spherical concave surface 33d of the inferior component 33b. In the various embodiments of this disclosure, the convex surfaces and the concave surfaces may be cylindrical, rectangular, elliptical, capsular, kidney-shaped, combinations thereof, and/or a variety of other non-spherical shapes. A non-spherical shape is understood to include any shape that does not have a uniform radius of curvature. In alternative embodiments of this disclosure, the superior component and the inferior component may have a spherical concave surface and/or the spacer may have a spherical convex surface.

The spacer 31 may be movably engaged with the superior and inferior components such that the surface 33c of the superior component 33a, for example, may slide and/or rotate with respect to the surface 31a of the spacer 31. In other embodiments of this disclosure, the spacer may be molded (i.e., attached) between the superior and inferior components.

The spacer 31, the superior component 33a, and the inferior component 33b work together to allow or limit motion of the superior component 33a with respect to the inferior component 33b. The motion is allowed or limited based on the elasticity of the spacer 31 and the shape of the convex surfaces 31a, 31b of the spacer 31 that articulate with the concave surfaces 33c, 33d of the superior component 33a and the inferior component 33b, respectively. Flexion-extension is allowed or limited by elastic deformation of the spacer 31 in conjunction with the articulation of the spacer 31 with the superior component 33a and the inferior component 33b. Lateral bending and rotation are allowed or limited mainly by elastic deformation of the spacer 31.

The artificial intervertebral joint of this embodiment is sufficiently compact so that it can be inserted via a bilateral posterior approach without sacrificing the facet joints. The artificial intervertebral joint of this embodiment may also be inserted via an anterior approach. Additionally, the artificial intervertebral joint of this embodiment is mechanically robust enough to provide support in the lumbar or cervical spine. Furthermore, the artificial intervertebral joint of this embodiment is flexible enough to allow a desirable range of motions with variable centers of rotation, yet is sufficiently durable under constant sheer and dynamic loading in the L5-S1 level. Although the embodiments of this disclosure may generally refer to the lumbar and sacral areas of the spine, it is understood that alternate embodiments of the artificial intervertebral joints may be used in the cervical and thoracic areas of the spine.

Figure 7:
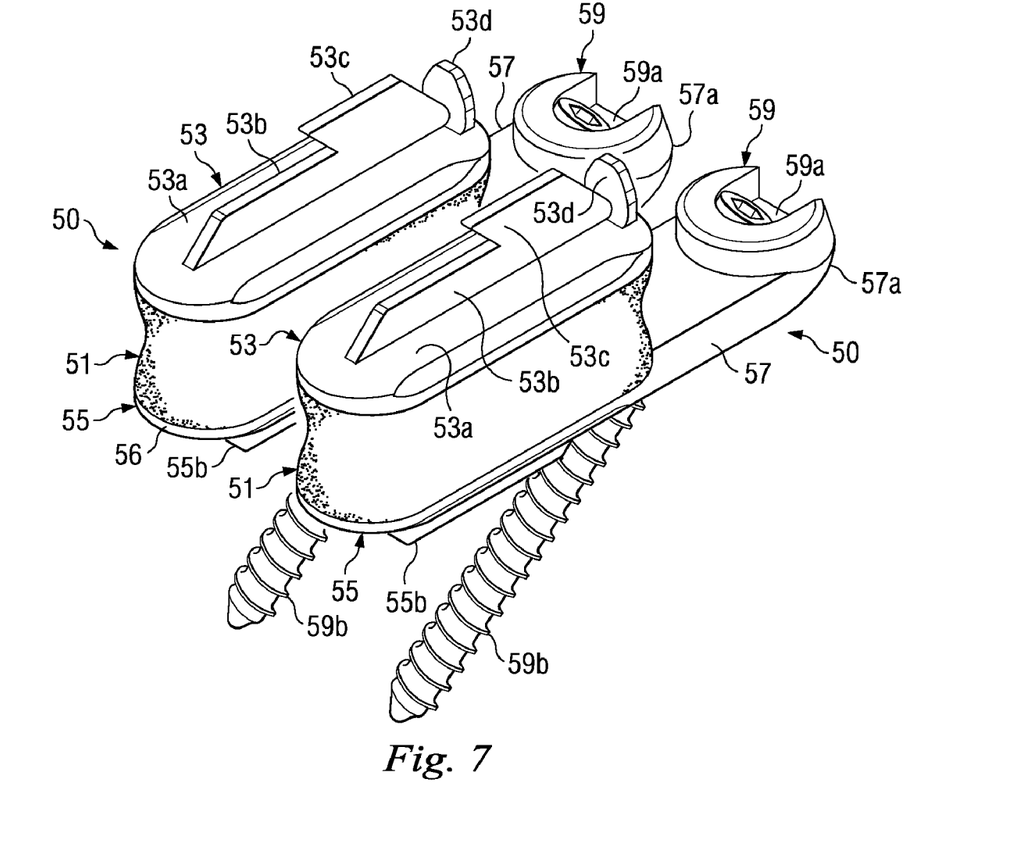
FIG. 7 is a perspective view of a portion of an artificial intervertebral joint constructed according to a second embodiment of the disclosure.
Figure 8:
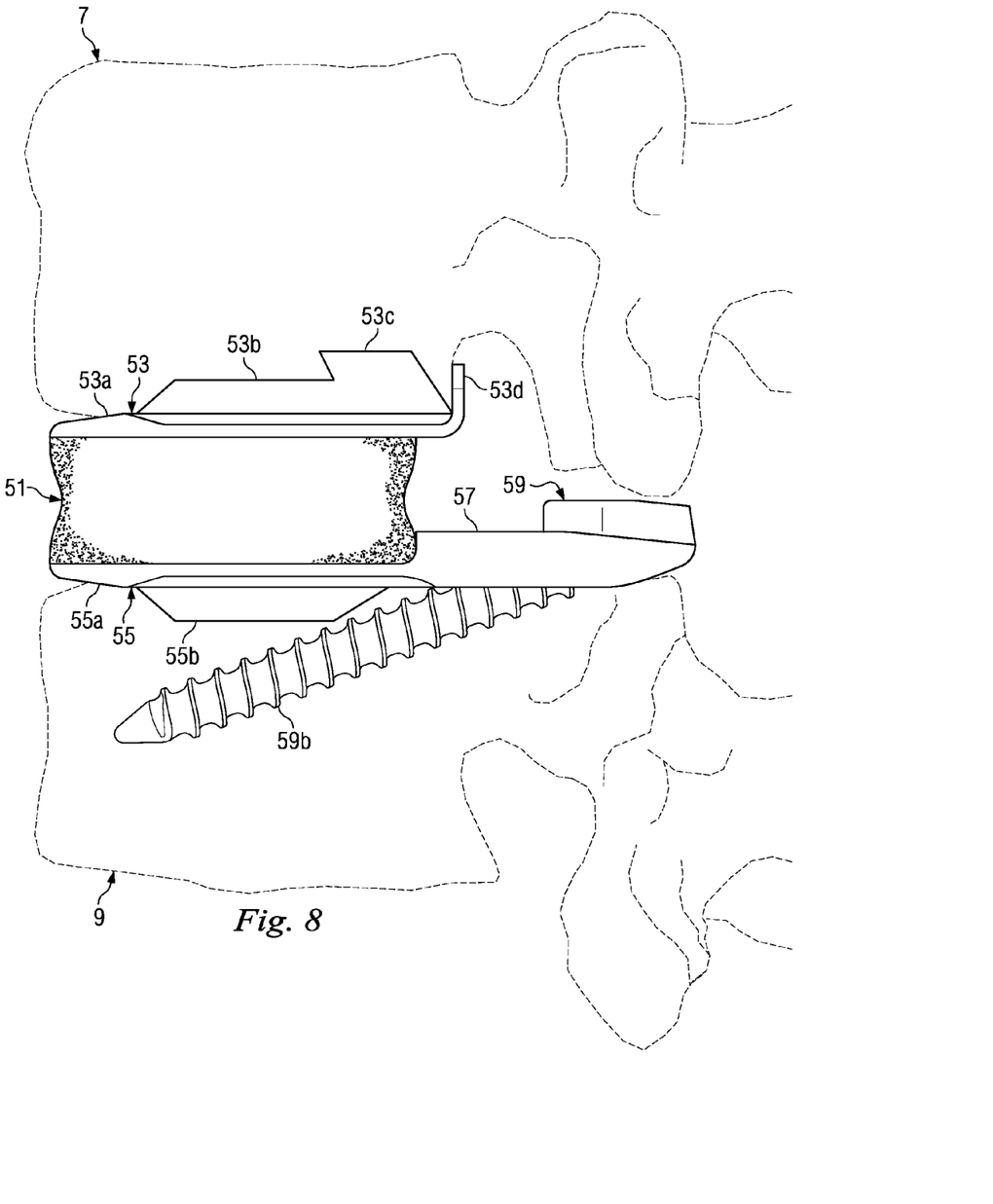
FIG. 8 is a side view of a portion of a lumbar spine showing the artificial intervertebral joint illustrated in FIG. 7.
Figure 9:
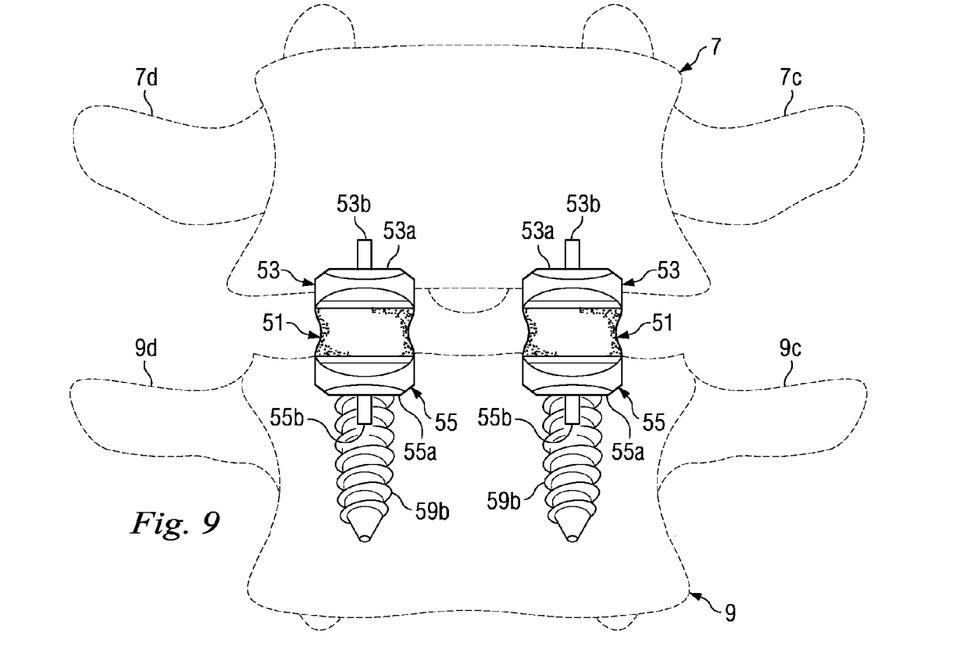
FIG. 9 is a front view of a lumbar spine showing the artificial intervertebral joint illustrated in FIGS. 7-8.
Figure 10:
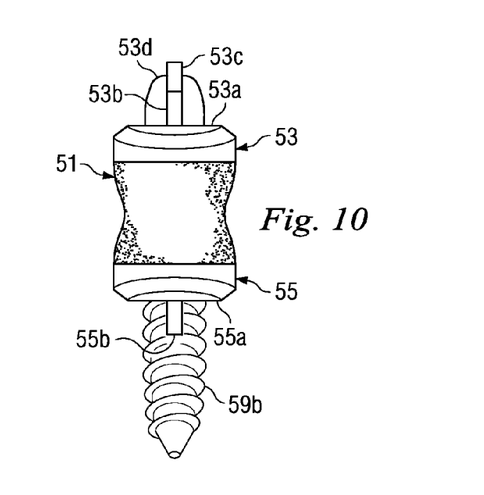
FIG. 10 is a front view of the artificial intervertebral joint illustrated in FIGS. 7-9.

FIGS. 7-10 illustrate a second exemplary embodiment of an artificial intervertebral joint. As illustrated in FIG. 7, each joint is composed of two arthroplasty subcomponents 50, each of which has a spacer 51, a superior component 53, and an inferior component 55. In the example illustrated in FIG. 7, the superior component 53 is superior to (above) the inferior component 55 and the spacer 51 is situated therebetween.

The inferior component 55 includes an anterior section 56 and a bridge 57 extending posteriorly from the anterior section 56. As installed, the bridge 57 may further extend posteriorly from the intervertebral disc space between the superior vertebral body 7a and the inferior vertebral body 9a and along at least a portion of a pedicle to a distal end 57a. In an alternative embodiment, all or a portion of a pedicle may be removed leaving the bridge with little or no support from natural structures. Additionally, in this embodiment, the bridge 57 couples the inferior component 55 to an attachment mechanism 59.

The superior component 53 and the inferior component 55 may be situated between two adjacent vertebrae. More particularly, the superior component 53 may be situated along an inferior surface of the superior vertebral body 7a and the anterior section 56 of the inferior component 55 may be situated on a superior surface of the inferior vertebral body 9a with the bridge 57 and the attachment mechanism 59 extending posteriorly from the disc space. However, it should be understood by one of ordinary skill in the art that the superior component, the inferior component, the bridge, and the attachment mechanism are not limited to such an arrangement, and may be oriented in different positions and/or shaped differently than what is illustrated herein.

In this embodiment, the attachment mechanism 59 includes a bone screw receptor 59a and a bone screw 59b, however in alternative embodiments, attachment mechanisms such as nails, staples, or other mechanical or chemical fasteners may be suitable. The orientation of the attachment mechanism 59 permits the bone screw 59b to become inserted extrapedicularly such that the bone screw 59b travels a path obliquely angled or skewed away from a central axis defined through a pedicle. The bone screw 59b may be threaded across a portion of the pedicle and into the inferior vertebral body 9a. Extrapedicular fixation may be any fixation into the pedicle that does not follow a path down a central axis defined generally posterior-anterior through the pedicle. In this embodiment, the bone screw 59b passes through an upper wall of a pedicle and may achieve strong cortical fixation. In some embodiments, the attachment mechanisms may be at least partially recessed so as not to interfere with articulations, soft tissues, and neural structures.

As installed, the bridge 57 and the attachment mechanism 59 may limit excessive movement of the artificial intervertebral joint, particularly during flexion/extension motions. Additionally, the bridge 57 may distribute loads on the inferior vertebra 9, reducing the potential for subsidence of the inferior component 55 into the inferior vertebra 9.

The superior component 53 includes a superior vertebra engaging surface 53a structured to engage the superior vertebral body 7a. Likewise, the inferior component 55 includes an inferior vertebra engaging surface 55a structured to engage the inferior vertebral body 9a. Additionally, the superior component 53 includes an optional superior keel 53b extending from the superior vertebra engaging surface 53a and the inferior component 55 includes an optional inferior keel 55b extending from the inferior vertebra engaging surface 55a to stabilize the arthroplasty. Additionally, the superior keel 53b includes a superior catch 53c so as to help further secure the superior component 53 to the superior vertebral body 7a. In this embodiment, the catch 53c includes a sharpened and undercut leading edge. Additionally, the superior keel and the inferior keel may include holes so as to promote bone ingrowth.

Furthermore, the superior component 53 includes a superior tab 53d extending upward from the posterior edge of the superior vertebra engaging surface 53a. In this embodiment, the superior tab 53d may be generally perpendicular or slightly acutely angled relative to the superior vertebra engaging surface 53a. The superior tab 53d may be integrally formed with or otherwise abut the posterior end of the superior keel 53b. The superior tab 53d may serve as a stop to prevent the artificial intervertebral joint of this disclosure from being inserted too far anteriorly into the intervertebral disc space. Once positioned in the spinal column, the superior tab 53d may engage the superior vertebral body 7a.

The spacer 51 has a dual modulus of elasticity, but may, in alternative embodiments, have a single modulus of elasticity or more than two moduli. The spacer 51 may be made of a single material or of multiple materials. The spacer 51 may have a gradual transition, or gradient change, between the dual moduli. Alternatively, a distinct change between the moduli may be suitable. In one example, ends of the spacer 51, disposed adjacent the superior component 53 and the inferior component 55, may have a higher modulus (i.e., stiffer) than the middle of the spacer 51, disposed in between the ends of the spacer 51. In another example, the core of the spacer 51 may have a higher modulus than the outer periphery of the spacer 51.

Gradual changes in gradient may be achieved through molding methods, including injection molding methods. Within a spacer formed of an otherwise homogeneous material, the modulus of elasticity may be varied by varying the amount and type of chemical crosslinking. The gradient changes may also result from combining or dispersing additional materials in varying amounts throughout an otherwise homogeneous material to achieve a desired combined or blended modulus. Modulus gradation can also result from the use of reinforcing materials. Furthermore, variations in gradation may be achieved through physical features such as changes in implant thickness, surface patterns, material porosity, or material voids.

The spacer 51 may be formed of elastomeric materials such as polyurethane, silicone, silicone polyurethane copolymers, polyolefins, such as polyisobutylene rubber and polyisoprene rubber, neoprene rubber, nitrile rubber, vulcanized rubber and combinations thereof. Certain portions of the implant, such as lower modulus regions, layers, or areas may be formed of more deformable or compliant materials including soft elastomers and polymeric gels.

The spacer 51, the superior component 53, and the inferior component 55 work together to allow or limit motion of the superior component 53 with respect to the inferior component 55. The artificial intervertebral joint of this embodiment may be inserted via a bilateral posterior approach. The dual moduli of the spacer 51 allows the spacer 51 to be stiff in axial compression while still providing a dampening effect. Also, the dual moduli of the spacer 51 allows the spacer 51 to be soft enough to allow motion in flexion/extension, axial rotation, and lateral bending. Additionally, the dual moduli of the spacer 51 will simulate the function of facet capsules and normal disc by providing increased resistance as range of motion increases. Compared to traditional ball and socket joints, the artificial intervertebral joint of this embodiment may result in lower wear debris, may allow a more natural motion during lateral bending and rotation, and may be less likely to lock up or come out of alignment.

Figure 11:
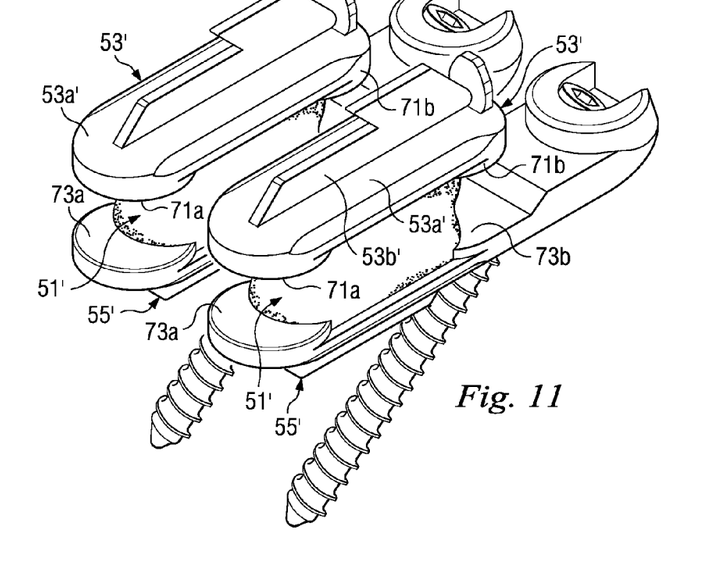
FIG. 11 is a perspective view of a third embodiment of an artificial intervertebral joint.
Figure 12:
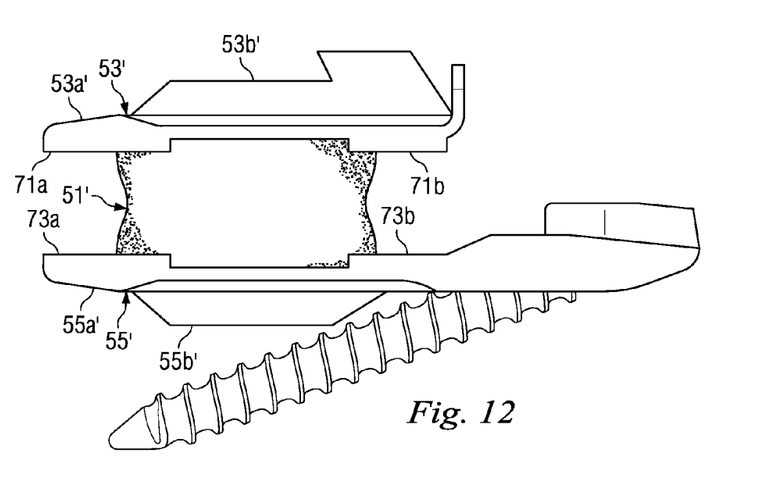
FIG. 12 is a side view of the artificial intervertebral joint illustrated in FIG. 11.

FIGS. 11-12 illustrate a third exemplary embodiment of an artificial intervertebral joint. Only features that differ from the second embodiment are discussed in detail herein. In the third embodiment, the superior component 53' includes a first superior shoulder 71a and a second superior shoulder 71b to engage the spacer 51' and to prevent dislocation of the spacer 51'. The first superior shoulder 71a and the second superior shoulder 71b extend from a surface opposing the superior vertebra engaging surface 53a'. The shoulders 71a, 71b may at least partially surround an upper portion of the spacer 51' to limit shearing forces and the lateral and/or anterior-posterior displacement of the spacer 51' relative to the superior component 53'. Similarly, the inferior component 55' includes a first inferior shoulder 73a and a second inferior shoulder 73b to engage the spacer 51' and to prevent dislocation of the spacer 51'. The first inferior shoulder 73a and the second inferior shoulder 73b extend from a surface opposing the inferior vertebra engaging surface 55a'. The shoulders 73a, 73b may at least partially surround a lower portion of the spacer 51' to limit lateral and/or anterior-posterior displacement of the spacer 51' relative to the inferior component 55'.

Figure 13:
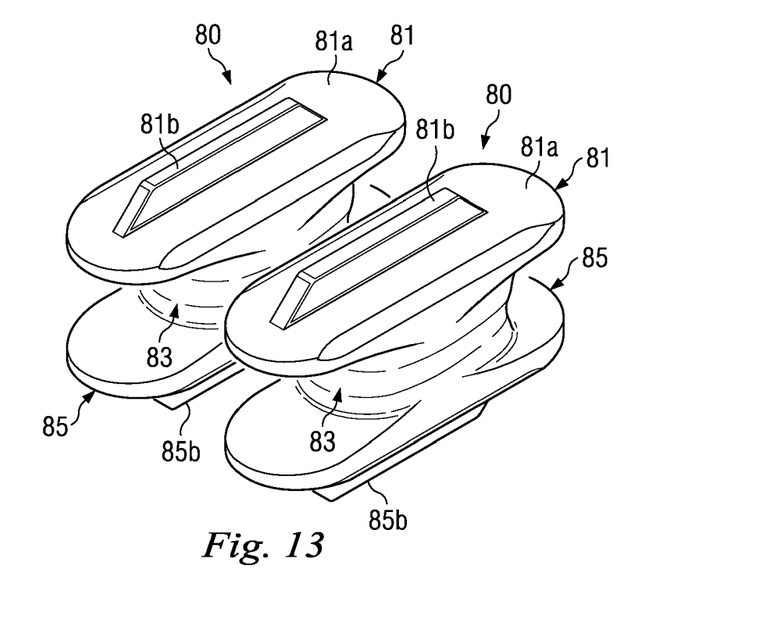
FIG. 13 is a perspective view of a fourth embodiment of an artificial intervertebral joint.
Figure 14:
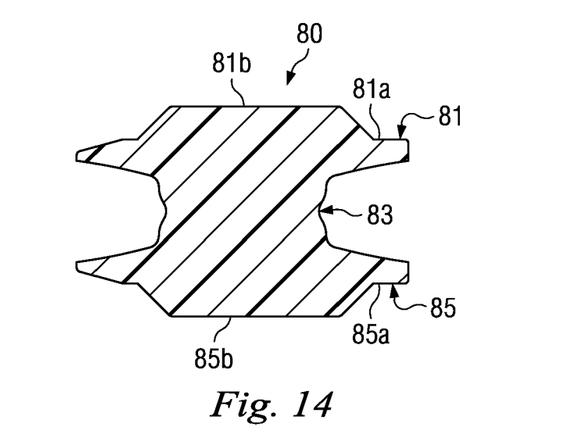
FIG. 14 is a cross-sectional view of the artificial intervertebral joint illustrated in FIG. 13.

FIGS. 13-14 illustrate a fourth exemplary embodiment of an artificial intervertebral joint. As illustrated in FIG. 13, each joint is composed of two arthroplasty subcomponents 80, each of which is a unitary polymeric device, illustrated best in FIG. 14. Each arthroplasty subcomponent 80 has a superior component 81, a connecting component 83, and an inferior component 85. In the example illustrated in FIGS. 13 and 14, the superior component 81 is superior to (above) the inferior component 85 and the connecting component 83 is connected therebetween. Although the artificial intervertebral joint according to this exemplary embodiment includes a pair of arthroplasty subcomponents, it should be understood that alternative embodiments may be implemented such that an artificial intervertebral joint includes a single arthroplasty subcomponent or more than two arthroplasty subcomponents. It should also be understood that alternative embodiments may also be carried out with arthroplasty subcomponents of unequal sizes.

The superior component 81 and the inferior component 85 may be situated between two adjacent vertebrae 7, 9. More particularly, the superior component 81 may be situated along an inferior surface of the superior vertebral body 7a and the inferior component 85 may be situated above a superior surface of the inferior vertebral body 9a. However, it should be understood by one of ordinary skill in the art that the superior component and the inferior component are not limited to such an arrangement, and may be oriented in different positions and/or shaped differently than what is illustrated herein.

The superior component 81 includes a superior vertebra engaging surface 81a structured to engage the superior vertebral body 7a. Likewise, the inferior component 85 includes an inferior vertebra engaging surface 85a structured to engage the inferior vertebral body 9a. Additionally, the superior component 81 includes an optional superior keel 81b extending from the superior vertebra engaging surface 81a and the inferior component 85 includes an optional inferior keel 85b extending from the inferior vertebra engaging surface 85a to stabilize the arthroplasty. Additionally, the superior keel 81b may include a superior catch so as to help further secure the superior component 81 to the superior vertebral body 7a. The superior keel 81b and the inferior keel 85b may include holes so as to promote bone ingrowth.

Although each arthroplasty subcomponent 80 is a unitary structure, its components may have differing material properties. Specifically, the superior component 81, the inferior component 85, and the connecting component 83 may have differing moduli of elasticity. For example, the superior component 81 may have at least one superior component modulus, the inferior component 85 may have at least one inferior component modulus, and the connecting component 83 may have at least one connecting component modulus. The superior component 81, the inferior component 85, and the connecting component 83 may be made of one material or multiple materials. For example, the connecting component 83 may include a gradual gradient change in modulus wherein ends of the connecting component 83, disposed adjacent the superior component and the inferior component 85, are a higher modulus (i.e., stiffer) than the center of the connecting component 83, disposed in between the ends of the connecting component 83. The superior component modulus 81 and the inferior component 85 modulus may be higher than the moduli of the connecting component 83. As such, the superior component 81 and the inferior component 85 may be more rigid than the connecting component 83.

Suitable materials for the superior, inferior, and connecting components may be elastic materials such as, for example, polyurethane, silicone or a silicone type elastomer, silicone polyurethane copolymers, a laminated composite polymer material, polyolefins, such as polyisobutylene rubber and polyisoprene rubber, neoprene rubber, nitrile rubber, vulcanized rubber and combinations thereof. Certain portions of the implant, such as lower modulus regions, layers, or areas may be formed of more deformable or compliant materials including soft elastomers and polymeric gels.

Gradual changes in gradient may be achieved through molding methods, including injection molding methods. Within a spacer formed of an otherwise homogeneous material, the modulus of elasticity may be varied by varying the amount and type of chemical crosslinking. The gradient changes may also result from combining or dispersing additional materials in varying amounts throughout an otherwise homogeneous material to achieve a desired combined or blended modulus. Modulus gradation can also result from the use of reinforcing materials. Furthermore, variations in gradation may be achieved through physical features such as changes in implant thickness, surface patterns, material porosity, or material voids.

The connecting component 83, the superior component 81, and the inferior component 85 work together to allow or limit motion of the superior component 81 with respect to the inferior component 85. The differing moduli between the components allow the connecting component 83 to be stiff in axial compression while still providing a dampening effect. Also, the connecting component modulus allows the connecting component 83 to be soft enough to allow motion in flexion/extension, axial rotation, and lateral bending. The differing moduli may function to simulate facet capsule and normal disc performance by providing increased resistance as range of motion increases. Compared to a traditional ball and socket joint (e.g., a hemispherical projection set in articulating engagement with a similarly sized hemispherical recess), the artificial intervertebral joint of this embodiment may result in lower wear debris, may allow a more natural motion during lateral bending and rotation, and may be less likely to lock up or come out of alignment. The artificial intervertebral joint of this embodiment may be inserted via a bilateral posterior approach.

Figure 15:
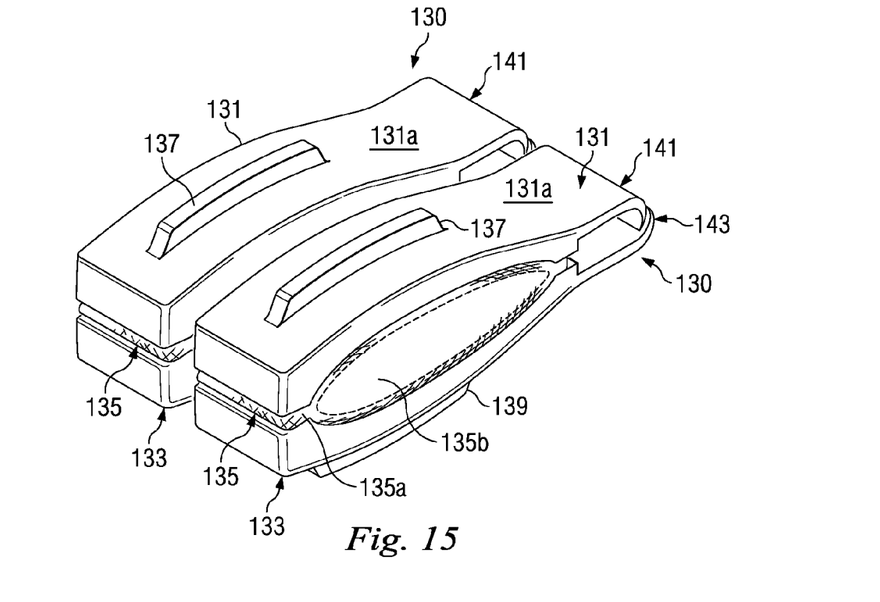
FIG. 15 is a perspective view of a fifth embodiment of an artificial intervertebral joint.
Figure 16:
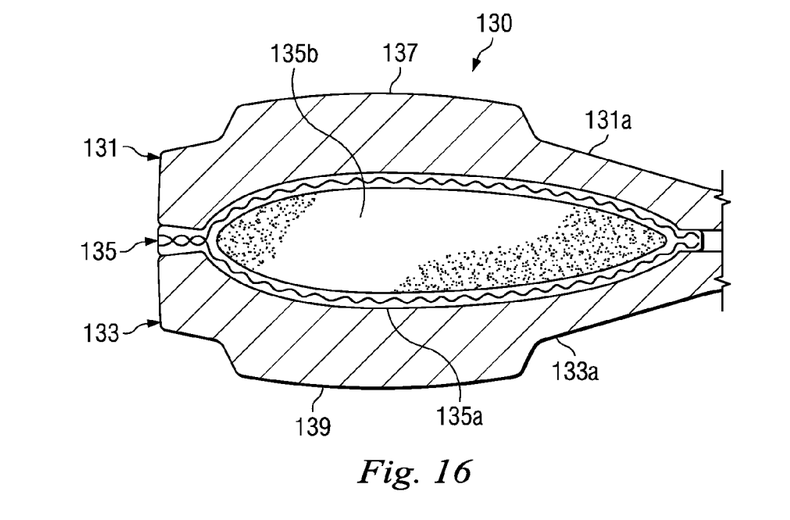
FIG. 16 is a cross-sectional view of the artificial intervertebral joint illustrated in FIG. 15.

FIGS. 15-17D illustrate a fifth exemplary embodiment of an artificial intervertebral joint. As illustrated in FIGS. 15-16, each joint is composed of two arthroplasty subcomponents 130, each of which has a superior component 131, an inferior component 133, and a mesh component 135. In the example illustrated in FIGS. 15-16, the superior component 131 is superior to (above) the inferior component 133 and the mesh component 135 is situated therebetween. Although the artificial intervertebral joint according to this exemplary embodiment includes a pair of arthroplasty subcomponents, it should be understood that alternative embodiments may be implemented such that an artificial intervertebral joint includes a single arthroplasty subcomponent or more than two arthroplasty subcomponents. It should also be understood that alternative embodiments may also be carried out with arthroplasty subcomponents of unequal sizes.

In this embodiment, the mesh component 135 is a separate component which is inserted between the superior component 131 and the inferior component 133. However, it should be understood that the mesh component 135 may be integrally formed with or integrated into one or both of the superior component 131 and the inferior component 133.

The superior component 131 and the inferior component 133 may be situated between two adjacent vertebrae 7, 9. More particularly, the superior component 131 may be situated along an inferior surface of the superior vertebral body 7a and the inferior component 133 may be situated above a superior surface of the inferior vertebral body 9a. However, it should be understood by one of ordinary skill in the art that the superior component and the inferior component are not limited to such an arrangement, and may be oriented in different positions and/or shaped differently than what is illustrated herein.

Additionally, the superior component 131 includes a superior vertebra engaging surface 131a structured to engage the superior vertebral body 7a. Likewise, the inferior component 133 includes an inferior vertebra engaging surface 133a structured to engage the inferior vertebral body 9a. Further, each of the superior component 131 and the inferior component 133 may be made from a rigid material that facilitates a connection to the superior vertebral body 7a and the inferior vertebral body 9a, respectively. Additionally, the superior component 131 includes an optional superior keel 137 and the inferior component 133 includes an optional inferior keel 139 to stabilize the arthroplasty. The superior keel 137 and the inferior keel 139 may include holes so as to promote bone ingrowth.

The surfaces of the superior component 131 and the inferior component 133 of the arthroplasty that contact the remaining endplates of the vertebrae may be coated with a beaded material or plasma sprayed to promote bony ingrowth and a firm connection therebetween. In particular, the surface to promote bone ingrowth may be a cobalt chromium molybdenum alloy with a titanium/calcium/phosphate double coating, a mesh surface, or any other effective surface finish. Alternatively or in combination, an adhesive or cement such as polymethylmethacrylate (PMMA) may be used to fix all or a portion of the components to one or both of the endplates.

In this embodiment, the mesh component 135 includes a mesh container 135a and a core 135b. As can be seen in FIGS. 15-16, the core 135b is contained within the mesh container 135a. The mesh container 135a includes interlacing fibers and may be made of a material such as, for example, metal, polymer, nylon, gortex, or any other suitable material. The mesh container 135a may be attached to the superior component 131 and/or the inferior component 133 by, for example, heat or a chemical melt. The mesh container 135a may be thicker at its anterior and posterior extremities to mimic the function of a natural annulus.

The core 135b may be made of an elastic and/or expandable material including, for example, silicone, latex, a polyolefin copolymer, polyethylene, polycarbonate, polyethylene terephthalate, a polyvinyl chloride, a styrenic resin, polypropylene, thermoplastic polyester, an elastomeric material, synthetic rubber, polyisobutylene, polyisopropene, neoprene, nitrile rubber, vulcanized rubber, a vulcanized copolymer, a thermoplastic polyurethane, an aliphatic polyurethane, an aromatic polyurethane, a segmented polyurethane, a hydrophilic polyurethane, polyether urethane, a polycarbonate-urethane, a silicone polycarbonate polyurethane, a silicone polyetherurethane, a thermoplastic elastomer, a polycarbonate, acrylonitrile-butadiene-styrene resin, acrylic, a polyurethane, nylon, a styrene acrylonitrile, a cellulosic, and/or any other suitable elastic or expandable material. In some embodiments, the core 135b may be an expandable balloon. In embodiments wherein the core 135b is made of an expandable material, the core 135b may expand once it is placed within a patient. The core 135b may have a reduced first form that fits into an opening of the mesh container 135a prior to expanding. The core 135b may be fluid while in the reduced first form and may have an initial viscosity to be delivered into the mesh container 135a after the mesh container 135a has been placed within the spinal column. The core 135b may cure once it is within the mesh container 135a and may not leak from the mesh container 135a once cured. The core 135b may cure and/or expand upon being placed within the mesh container 135a, or alternatively, the core 135b may cure and/or expand by having a biomaterial injected into the core 135b.

The core 135b of this embodiment may be sufficiently compact such that it may be inserted using a minimally invasive space. Once the artificial intervertebral joint is positioned within the spinal column, the core 135b may be expanded so as to retain a substantially rigid shape capable of maintaining a spacing between the superior component 131 and the inferior component 133.

The superior component 131 and the inferior component 133 include a superior posterior element 141 and an inferior posterior element 143, respectively. In this embodiment the superior posterior element 141 curves downwardly and the inferior posterior element 143 curves upwardly. An outer surface of the superior posterior element 141 may slidably engage an inner surface of the inferior posterior element 143. In other words, the superior posterior element 141 may engage and articulate with the inferior posterior element 143 to create a joint that mimics, at least in part, the behavior of a natural facet joint. The described arrangement of the elements 141, 143 may further prevent the superior component 131 from becoming displaced in a posterior direction.

Figure 17A:
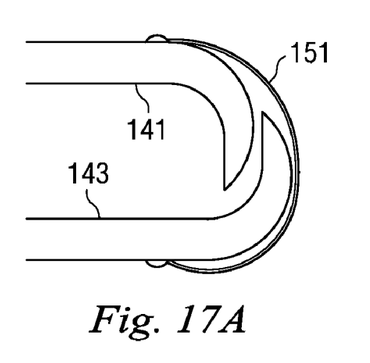
FIGS. 17A-17D illustrate side views of alternative posterior ends of the artificial intervertebral joint illustrated in FIGS. 15-16.
Figure 17B:
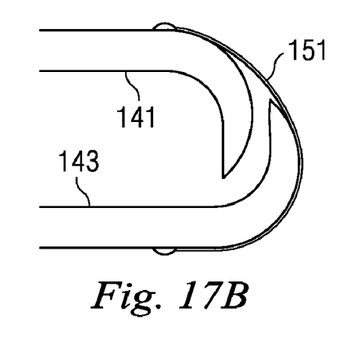
Figure 17C:
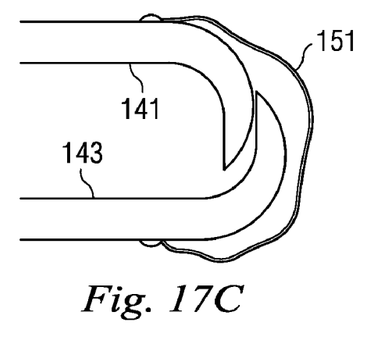
Figure 17D:
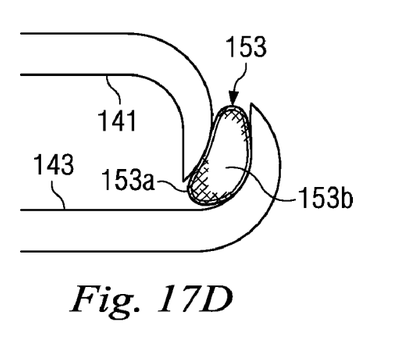

In various embodiments, the superior posterior element 141 and the inferior posterior element 143 may be coupled in a variety of configurations, as illustrated in FIGS. 17A-17D. FIGS. 17A-17C illustrate the superior posterior element 141 and the inferior posterior element 143 coupled by a restraint such as tether 151 while the spinal column is in a variety of positions. FIG. 17A illustrates the posterior elements 141, 143 while the artificial intervertebral joint is located in a spinal column that is in a neutral position. FIG. 17B illustrates the posterior elements 141, 143 while the artificial intervertebral joint is located in a spinal column that is in flexion. As can be seen in FIGS. 17A-17B, the tether 151 is tighter when the spinal column is in flexion than when the spinal column is in the neutral position. FIG. 17C illustrates the posterior elements 141, 143 while the artificial intervertebral joint is located in a spinal column that is in extension. As can be seen in FIGS. 17B-17C, the tether 151 is looser when the spinal column is in extension than when the spinal column is in flexion. FIG. 17D illustrates an alternative embodiment where the superior posterior element 141 and the inferior posterior element 143 are coupled by a further mesh component 153. The further mesh component 153 includes a further mesh container 153a and a further core 153b including similar materials and functionality as the mesh container 135a and the core 135b, respectively, discussed above with reference to FIGS. 15-16.

In other alternative embodiments, the superior posterior element 141 and the inferior posterior element 143 may be coupled by other restraints such as a mesh bag encapsulating the superior posterior element 141 and the inferior posterior element 143. When the superior posterior element 141 and the inferior posterior element 143 are encapsulated by the mesh bag, the mesh bag may limit the motion of the superior posterior element 141 with respect to the inferior posterior element 143 in a manner similar to the tether 151 of FIGS. 17A-17C and the further mesh component 153 of FIG. 17D. In other embodiments, the superior component 131 and the inferior component 133 may be completely encapsulated by a bag which may be non-porous or partially porous (e.g., a mesh). The bag may also contain a lubricating material (i.e., a fluid or gel).

The mesh component 135, the superior component 131, and the inferior component 133 work together to allow or limit motion of the superior component 131 with respect to the inferior component 133. The motion may be allowed or limited based on the elasticity and/or shape of the core 135b and/or the coupling of the superior posterior element 141 and the inferior posterior element 143. The result may be an improved center of rotation and transition of motion at adjacent levels of vertebra, and may decrease the likelihood that placement of the artificial intervertebral joint of this disclosure within the spinal column damages discs above or below the placement. Additionally, the mesh container 135a may be flexible and may absorb/store force/energy that is transferred from the core 135b to the mesh container 135a (i.e., hoop stress).

Again, these exemplary embodiments are merely illustrative and are not meant to be an exhaustive list of all possible designs, implementations, modifications, and uses of the invention. Moreover, features described in connection with one embodiment of the disclosure may be used in conjunction with other embodiments, even if not explicitly stated above.

While it should be readily apparent to a skilled artisan from the discussion above, a brief description of a suitable surgical procedure that may be used to implant the artificial joint is provided below. Generally, as discussed above, an embodiment of the artificial intervertebral joint may be implanted into a body using a posterior transforaminal approach similar to the known TLIF or PLIF procedures. According to this approach, an incision, such as a midline incision, may be made in the patient's back and some or all of the affected disc and surrounding tissue may be removed via the foramina. Depending on whether any of the facet joints are being replaced, the natural facet joints may be trimmed to make room for the artificial facet joints. Then, the subcomponents of the artificial intervertebral joint may be inserted piecewise through the left and right transforaminal openings, respectively. That is, the pieces of the artificial intervertebral joint including the upper and lower retaining portions, with or without facet components, and the artificial disc, if provided separately, fit through the foramina and are placed in the appropriate intervertebral space. The pieces of the artificial joint may be completely separated or two or more of them may be tied or packaged together prior to insertion through the foramina by cloth or other materials known in the art. In cases where at least a portion of the outer annulus of the natural disc can be retained, the lower retaining portions of each side of the artificial intervertebral joint are inserted such that they abut a corresponding portion of the annulus. If a midline anterior connection is provided, the left and right subcomponents of the retaining members are fitted together and held in place by the outer annulus. As such, the remaining portion of the annulus may be in substantially the same place as it was prior to the procedure.

Further, in the cases where the annulus of the natural disc must be removed completely or there is insufficient annulus remaining, it is possible, for example, to use the second exemplary embodiment of the disclosure wherein the pedicle screws are implemented so as to be assured that the pieces of the artificial intervertebral joint remain in place. It should be understood by one of ordinary skill in the art that the artificial joint could be implanted via an anterior approach or a combined anterior and posterior approach, although the advantages of a posterior procedure would be limited. For example, some of the pieces of the artificial intervertebral joint may be inserted from an anterior approach and others posteriorly.

The various embodiments of artificial intervertebral joints disclosed herein may be installed between the vertebrae 7, 9. Generally, the artificial intervertebral joint may be implanted into a body using a posterior transforaminal approach similar to the known TLIF or PLIF procedures. PLIF approaches are generally more medial and rely on more retraction of the traversing root and the exiting root to access the vertebral interspace. The space between these structures is known as Kambin's triangle. TLIF approaches are typically more oblique, requiring less retraction of the exiting root, and less epidural bleeding with less retraction of the traversing structures. It is also possible to access the interspace using a far lateral approach, above the position of the exiting nerve root and outside of Kambin's triangle. In some instances it is possible to access the interspace via the far lateral without resecting the facets. Furthermore, a direct lateral approach through the psoas is known. This approach avoids the posterior neural elements completely. Embodiments of the current invention are anticipated that could utilize any of these common approaches.

According to at least one of these approaches, an incision, such as a midline incision, may be made in the patient's back and some or all of the affected disc and surrounding tissue may be removed via the foramina. The superior endplate surface of the inferior vertebra 9 may be milled, rasped, or otherwise resected to match the profile of the inferior vertebra engaging surface, to normalize stress distributions on the superior endplate surface of the inferior vertebra 9, and/or to provide initial fixation prior to bone ingrowth. The preparation of the endplate of inferior vertebra 9 may result in a flattened surface or in surface contours such as pockets, grooves, or other contours that may match corresponding features on the inferior vertebra engaging surface. The inferior endplate of the superior vertebra 7 may be similarly prepared to receive the superior vertebra engagement surface. Depending on whether any of the facet joints are being replaced, the natural facet joints of vertebrae 7, 9 may be trimmed to make room for the artificial intervertebral joint.

The subcomponents of the artificial intervertebral joint may then be inserted piecewise through the left and right transforaminal openings, respectively. That is, the pieces of the artificial intervertebral joint including the superior and inferior components respectively fit through the foramina and are placed in the appropriate intervertebral disc space between the generally cylindrical bodies 7a, 9a. The pieces of the artificial joint may be completely separated or two or more of them may be tied or packaged together prior to insertion through the foramina by cloth or other materials known in the art. In cases where at least a portion of the outer annulus of the natural disc can be retained, the inferior components of each side of the artificial intervertebral joint are inserted such that they abut a corresponding portion of the annulus.

Additionally, it is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

What is claimed is:

1. An artificial vertebral joint for interposition between a superior vertebra and an inferior vertebra, said artificial vertebral joint comprising:
   a pair of bilateral joint subcomponents, each joint subcomponent including,
   a superior component including a superior vertebra engaging surface and a superior spacer engaging surface and further including a superior posterior element sized to extend posteriorly from between vertebral bodies of the superior and inferior vertebrae;
   an inferior component including an inferior vertebra engaging surface and an inferior spacer engaging surface and further including an inferior posterior element sized to extend posteriorly from between vertebral bodies of the superior and inferior vertebrae, wherein the superior posterior element is configured to engage and articulate with the inferior posterior element;

a spacer extending between the superior component and the inferior component, the spacer including a mesh container and a core contained within the mesh container; and a restraint extending between the superior and inferior posterior elements, wherein the restraint is a mesh bag.

2. An artificial vertebral joint for interposition between a superior vertebra and an inferior vertebra, said artificial vertebral joint comprising:

a pair of bilateral joint subcomponents, each joint subcomponent including, a superior component including a superior vertebra engaging surface and a superior spacer engaging surface and further including a superior posterior element sized to extend posteriorly from between vertebral bodies of the superior and inferior vertebrae;

an inferior component including an inferior vertebra engaging surface and an inferior spacer engaging surface and farther including an inferior posterior element sized to extend posteriorly from between vertebral bodies of the superior and inferior vertebrae, wherein the superior posterior element is configured to engage and articulate with the inferior posterior element;

a spacer extending between the superior component and the inferior component, the spacer including a first mesh container and a core contained within the first mesh container; and a restraint extending between the superior and inferior posterior elements, wherein the restraint is a second mesh container containing an elastomeric material.

3. The artificial vertebral joint of claim 1, wherein the spacer, the superior component, and the inferior component are an integrally formed unit.

4. The artificial vertebral joint of claim 1, wherein the spacer is slidably engaged with the superior and inferior components.

5. The artificial vertebral joint of claim 1, wherein the spacer is fixedly attached between the superior and inferior components.

6. The artificial vertebral joint of claim 1, wherein the superior component includes a keel extending from the superior vertebra engaging surface.

7. The artificial vertebral joint of claim 1, wherein the inferior component includes a bridge sized to extend posteriorly from between vertebral bodies of the superior and inferior vertebrae.

8. The artificial vertebral joint of claim 1, wherein either the superior or the inferior component includes a shoulder extending at least partially around the periphery of the spacer.

9. The artificial vertebral joint of claim 1, wherein the core includes a balloon.

10. The artificial vertebral joint of claim 1, wherein the spacer is expandable with the injection of a fluid material into the core.

11. The artificial vertebral joint of claim 1, wherein the core includes, an elastomeric material.

12. The artificial vertebral joint of claim 1, wherein the superior component includes a superior posterior element sized to extend posteriorly from between vertebral bodies of the superior and inferior vertebrae and the inferior component includes an inferior posterior element sized to extend posteriorly from between vertebral bodies of the superior and inferior vertebrae, wherein the superior posterior element is configured to engage and articulate with the inferior posterior element.

13. The artificial vertebral joint of claim 1, wherein the restraint extends between the superior and inferior posterior elements.

14. The artificial vertebral joint of claim 1, wherein the restraint is a tether.

15. The artificial vertebral joint of claim 2, wherein the spacer is slidably engaged with the superior and inferior components.

16. The artificial vertebral joint of claim 2, wherein the spacer is fixedly attached between the superior and inferior components.

17. The artificial vertebral joint of claim 2, wherein the superior component includes a keel extending from the superior vertebra engaging surface.

18. The artificial vertebral joint of claim 2, wherein the inferior component includes a bridge sized to extend posteriorly from between vertebral bodies of the superior and inferior vertebrae.

19. The artificial vertebral joint of claim 2, wherein the restraint extends between the superior and inferior posterior elements.

20. The artificial vertebral joint of claim 2, wherein either the superior or the inferior component includes a shoulder extending at least partially around the periphery of the spacer.

21. The artificial vertebral joint of claim 2, wherein the core includes a balloon.

22. The artificial vertebral joint of claim 2, wherein the spacer is expandable with the injection of a fluid material into the core.

23. The artificial vertebral joint of claim 2, wherein the core includes an elastomeric material.

24. The artificial vertebral joint of claim 2, wherein the spacer, the superior component, and the inferior component are an integrally formed unit.

25. The artificial vertebral joint of claim 2, wherein the superior component includes a superior posterior element sized to extend posteriorly from between vertebral bodies of the superior and inferior vertebrae and the inferior component includes an inferior posterior element sized to extend posteriorly from between vertebral bodies of the superior and inferior vertebrae, wherein the superior posterior element is configured to engage and articulate with the inferior posterior element.

* * * * *